US012605062B1

(12) United States Patent
El Beheiry et al.

(10) Patent No.: US 12,605,062 B1
(45) Date of Patent: Apr. 21, 2026

(54) SWITCHABLE AUTOSTEREOSCOPIC DISPLAY SYSTEM AND METHOD TO DISPLAY IMAGES THEREON

(71) Applicant: AVATAR MEDICAL, Paris (FR)

(72) Inventors: Mohamed El Beheiry, Paris (FR); Elodie Brient-Litzler, Paris (FR); Quentin Petit, Paris (FR); Nicolas Philippon, Paris (FR)

(73) Assignee: Avatar Medical, Paris (FR)

( * ) Notice: Subject to any disclaimer, the term of this patent is extended or adjusted under 35 U.S.C. 154(b) by 0 days.

(21) Appl. No.: 19/355,716

(22) Filed: Oct. 10, 2025

(51) Int. Cl.
| | |
|---|---|
| *A61B 3/00* | (2006.01) |
| *A61B 3/113* | (2006.01) |
| *G06T 7/00* | (2017.01) |
| *H04N 13/117* | (2018.01) |
| *H04N 13/261* | (2018.01) |
| *H04N 13/302* | (2018.01) |
| *H04N 13/359* | (2018.01) |
| *H04N 13/383* | (2018.01) |

(52) U.S. Cl.
CPC ............ *A61B 3/0058* (2013.01); *A61B 3/113* (2013.01); *G06T 7/0012* (2013.01); *H04N 13/117* (2018.05); *H04N 13/261* (2018.05); *H04N 13/302* (2018.05); *H04N 13/359* (2018.05); *H04N 13/383* (2018.05); *G06T 2207/10021* (2013.01); *G06T 2207/30041* (2013.01); *G06T 2215/00* (2013.01)

(58) Field of Classification Search
CPC ..... A61B 3/0058; A61B 3/113; G06T 7/0012; H04N 13/117; H04N 13/261; H04N 13/302; H04N 13/359; H04N 13/383
See application file for complete search history.

(56) References Cited

U.S. PATENT DOCUMENTS

| | | |
|---|---|---|
| 10,888,402 B2 | 1/2021 | Kim et al. |
| 11,995,847 B2 | 5/2024 | Aguirre-Valencia et al. |

FOREIGN PATENT DOCUMENTS

| | | |
|---|---|---|
| EP | 2375576 A1 | 10/2011 |
| WO | 2018066765 A1 | 4/2018 |
| WO | 2021155290 A1 | 8/2021 |
| WO | 2022177883 A2 | 8/2022 |

*Primary Examiner* — Jack Dinh
(74) *Attorney, Agent, or Firm* — Wood, Phillips, Katz, Clark & Mortimer

(57) ABSTRACT

The present invention relates to a method for displaying, on an autostereoscopic display system comprising a switchable autostereoscopic display, a composed stereoscopic image providing a 3D rendering to said user with a resolution of N pixels and a 2D image providing a flat rendering to said user at a higher resolution than the composed stereoscopic image.

15 Claims, 6 Drawing Sheets

1

SWITCHABLE AUTOSTEREOSCOPIC DISPLAY SYSTEM AND METHOD TO DISPLAY IMAGES THEREON

FIELD OF INVENTION

The present invention relates to a computer-implemented method for displaying, on an autostereoscopic display system comprising a switchable autostereoscopic display, a 3D representation and a 2D representation of at least one portion of a patient.

The invention further relates to an autostereoscopic display system.

BACKGROUND OF INVENTION

Stereoscopic vision provides the ability to perceive depth and relief. It allows assessing the distance of objects and understanding their three-dimensional shape. This is useful in the medical domain wherein part of the patient can be modelized in 3D and displayed by creating a depth rendering to the surgeon or physician which is able to better visualize the anatomy of the patient as it would be in the real world.

Stereoscopic vision devices comprise various approaches designed to provide each eye with different images to create a perception of depth. Known systems include glasses-based solutions using polarizing filters or active shutter glasses, which are widely employed in combination with stereoscopic displays and projectors. While technically mature, these solutions have the drawback of requiring additional eyewear.

Other devices rely on so-called autostereoscopic techniques, in which lenticular lenses or parallax barriers are arranged in front of the display to separate the images intended for each eye. Such devices allow viewing without glasses, but the image resolution is halved since two images must be displayed on the screen: one for each eye.

There is thus a need for a system and a display method for displaying images with a depth rendering to the user without requiring the user to wear glasses (i.e., glasses-free) while providing a higher resolution for displaying a flat rendering image.

SUMMARY

This invention thus relates to a computer-implemented method for displaying, on an autostereoscopic display system comprising a switchable autostereoscopic display, an image based on a 3D representation of at least one portion of a patient, said switchable autostereoscopic display configured to display at least 2×N pixels and being adapted to be switched between at least one stereoscopic configuration and a monoscopic configuration, said method comprising:
  receiving a 3D representation of at least one portion of a patient;
  determining if the autostereoscopic display is to operate in the stereoscopic configuration or in the monoscopic configuration, and:
  if the autostereoscopic display is determined to operate in the stereoscopic configuration, switching the autostereoscopic display to the stereoscopic configuration, and:
    determining, for each eye of a user, a viewing position of said eye relative to the autostereoscopic display;
    computing a pair of 2D images, each 2D image of the pair of 2D images being computed based on said 3D representation viewed respectively from each viewing position, each 2D image of the pair of 2D images being composed of N pixels;
    creating, using said pair of 2D images, a composed image by combining the pixels of the 2D images of the pair of 2D images;
    displaying said composed image on the autostereoscopic display in the at least one stereoscopic configuration thereby providing a depth rendering of the composed image to said user;
  if the autostereoscopic display is determined to operate in the monoscopic configuration, switching the autostereoscopic display to the monoscopic configuration, and:
    computing a single 2D image composed of 2×N pixels based on said 3D representation;
    displaying the single 2D image on the autostereoscopic display in the monoscopic configuration thereby providing a flat rendering of the at least one portion of the patient to said user at a higher resolution than the composed image.

Advantageously, this makes it possible to display a depth rendering image with a given resolution for each eye of a user and to display a flat-rendered image with double that resolution. The user may thus choose between the depth rendering or the flat rendering with the increased resolution, according to the visualization needs.

According to an advantageous embodiment, the invention comprises at least one of the following features taken alone or in combination:

The method further comprises, when the autostereoscopic display is switched to operate in the stereoscopic configuration, tracking positions of the eyes of the user to determine, for each eye, the viewing position of said eye relative to the autostereoscopic display over time, wherein the composed image is repeatedly updated and displayed according to changes in the viewing position of each eye relative to the autostereoscopic display.

The single 2D image is computed and displayed on an additional 2D display comprised in the autostereoscopic system, the computing and the displaying of the single 2D image being simultaneous and synchronous with the computing and the displaying of the composed image on the autostereoscopic display.

The method further comprises displaying on the autostereoscopic display in the at least one stereoscopic configuration, a flat rendering of a cross-sectional image associated to the 3D representation alongside the depth rendering of the 3D representation.

Displaying a flat rendering of a cross-sectional image comprises:
  receiving a cross-sectional image associated to said 3D representation of at least one portion of a patient;
  computing twin images of the cross-sectional image;
  computing a multi-rendering image by combining said twin images of the cross-sectional image and the pair of images forming the composed image;
  displaying the multi-rendered image using the autostereoscopic display in the at least one stereoscopic configuration.

Displaying a flat rendering of a cross-sectional image comprises:
  receiving a cross-sectional image associated to said 3D representation of at least one portion of a patient;
  computing twin images of the cross-sectional image;
  creating, from the twin images, a composed flat image which, when displayed on the autostereoscopic display

3 in the at least one stereoscopic configuration provides the flat rendering to the user;

displaying the composed image next to the composed flat image on the autostereoscopic display in the at least one stereoscopic configuration.

The flat rendering of the cross-sectional image and the composed image are associated to a common scene coordinate system, the method further comprising:

displaying, over the flat rendering of the cross-sectional image, a representation of a cursor, and updating, upon selection with said cursor of at least one pixel within the flat rendering of the cross-sectional image, the composed image based on selected pixels by:

computing a pair of updated images, each updated image of the pair of updated images being computed based on said 3D representation viewed from each viewing position, each updated image of the pair of updated images being composed of N pixels;

creating, using the pair of updated images, a composed updated image by combining the pixels of the two updated images of the pair of updated images;

displaying the composed updated image on the autostereoscopic display in the stereoscopic configuration;

and optionally:

computing a single 2D updated image composed of $2 \times N$ pixels based on said 3D representation;

displaying the single 2D updated image on the autostereoscopic display in the monoscopic configuration.

Updating the composed image comprises adding, in the composed image, a graphical element by:

computing a pair of updated images comprising the graphical element, each updated image of the pair of updated images being computed based on said 3D representation viewed from each viewing position, each updated image of the pair of updated images being composed of N pixels;

creating, using the pair of updated images, a composed updated image by combining the pixels of the two updated images of the pair of updated images;

displaying the composed updated image on the autostereoscopic display in the stereoscopic configuration;

and by optionally:

computing a single 2D updated image based on said 3D representation comprising the graphical element, the single 2D updated image being composed of $2 \times N$ pixels;

displaying the single 2D updated image on the autostereoscopic display in the monoscopic configuration.

Two pixels are selected and wherein the graphical element is a representation of a 3D distance between said two pixels.

The 3D representation of at least one portion of a patient is computed by applying a volume rendering technique on a 3D image of the at least one portion of the patient, and wherein updating the composed image comprises generating the 3D representation by modifying parameters of the volume rendering technique based on said selection of at least one pixel within the flat rendering of the cross-sectional image.

The selection of at least one pixel within the flat rendering of the cross-sectional image comprises automatically selecting a set of pixels comprising the pixel selected using the cursor and at least one neighboring pixel, the method further comprising:

computing a pair of updated images wherein the set of pixels are highlighted, each updated image of the pair of images being computed based on said 3D representation viewed from each viewing position, each updated image of the pair of updated images comprising N pixels;

creating, using the pair of updated images, a composed updated image by combining the pixels of the two updated images of the pair of updated images;

displaying the composed updated image on the autostereoscopic display in the stereoscopic configuration;

and optionally:

computing a single 2D updated image based on said 3D representation wherein the set of pixels are highlighted, the single 2D updated image comprising $2 \times N$ pixels;

displaying the single 2D updated image on the autostereoscopic display in the monoscopic configuration.

This invention also relates to a non-transitory program storage device, readable by a computer, tangibly embodying a program of instructions executable by the computer to perform the method according to the disclosure.

This invention also relates to an autostereoscopic display system comprising:

a switchable autostereoscopic display configured to display $2 \times N$ pixels and able to switch between at least one stereoscopic configuration and a monoscopic configuration;

an eye tracking system configured for real-time tracking of a viewing position of each eye of a user;

an input for receiving a 3D representation of at least one portion of a patient;

a processor configured for:

computing a pair of images, each image of the pair of images being computed based on said 3D representation viewed respectively from each viewing position, each image of the pair of images being composed of N pixels;

creating, using said pair of images, a composed image by combining the pixels of the images of the pair of images;

computing a single 2D image comprising $2 \times N$ pixels based on said 3D representation;

an output configured for:

displaying the composed image on the autostereoscopic display in the stereoscopic configuration thereby creating a depth rendering of the composed image to said user;

displaying the single 2D image on the autostereoscopic display in the monoscopic configuration thereby providing a flat rendering to the user at a higher resolution than the composed image.

According to an advantageous embodiment, the autostereoscopic display system further comprises a 2D display configured for displaying the single 2D image According to an advantageous embodiment, the autostereoscopic display and the 2D display can be arranged to be both in a field of view of a single user In addition, the disclosure relates to a computer program comprising software code adapted to perform a method for displaying, on an autostereoscopic display system comprising a switchable autostereoscopic display, a 3D and a 2D representation of at least one portion of a patient compliant with any of the above execution modes when the program is executed by a processor.

The present disclosure further pertains to a non-transitory program storage device, readable by a computer, tangibly embodying a program of instructions executable by the computer to perform a method for displaying, on an autostereoscopic display system comprising a switchable autostereoscopic display, a 3D representation of at least one portion of a patient compliant with the present disclosure.

Such a non-transitory program storage device can be, without limitation, an electronic, magnetic, optical, electro-magnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Eras-able Programmable ROM) or a Flash memory, a portable CD-ROM (Compact-Disc ROM).

Definitions

In the present invention, the following terms have the following meanings:

The terms "adapted" and "configured" are used in the present disclosure as broadly encompassing initial configu-ration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The proces-sor may also encompass one or more Graphics Processing Units (GPU), whether exploited for computer graphics and image processing or other functions. Additionally, the instructions and/or data enabling to perform associated and/or resulting functionalities may be stored on any pro-cessor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

The terms "autostereoscopic display" designates a display capable of displaying a stereoscopic image without requiring the viewer to wear glasses.

The terms "switchable autostereoscopic display" desig-nates an autostereoscopic display capable of being switched between a stereoscopic configuration and a monoscopic configuration.

The terms "monoscopic configuration" designate the con-figuration into which a switchable autostereoscopic display displays an image without activating the stereoscopic con-figuration.

By a "3D image" of a subject or object, one has to understand an image of said subject or object as acquired by an imaging device providing 3D images, such as for example a CT-Scanner, an MRI imager, a 3D intraoral dental scanner, etc. . . . . A 3D image is generally in the form of a 3D matrix of pixel data (sometimes called voxels in such case).

By a "3D representation" of a subject or object, one has to understand a mathematical model of said subject or object, such as for example a vectorized 3D model as generated from a 3D pixel-based image for example.

BRIEF DESCRIPTION OF THE DRAWINGS

The present disclosure will be better understood, and other specific features and advantages will emerge upon reading the following description of particular and non-

Figure 1:
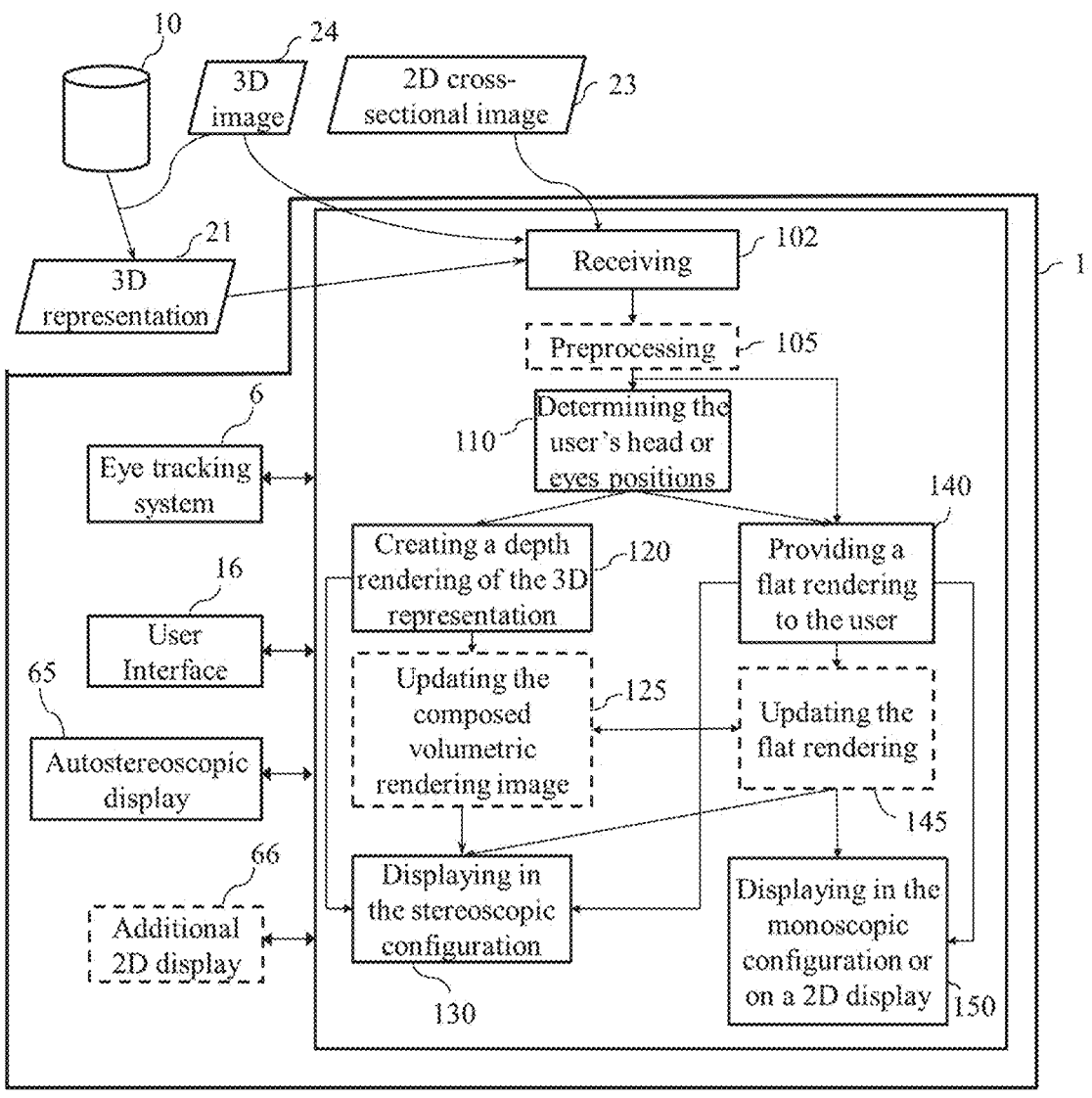
Figure 2:
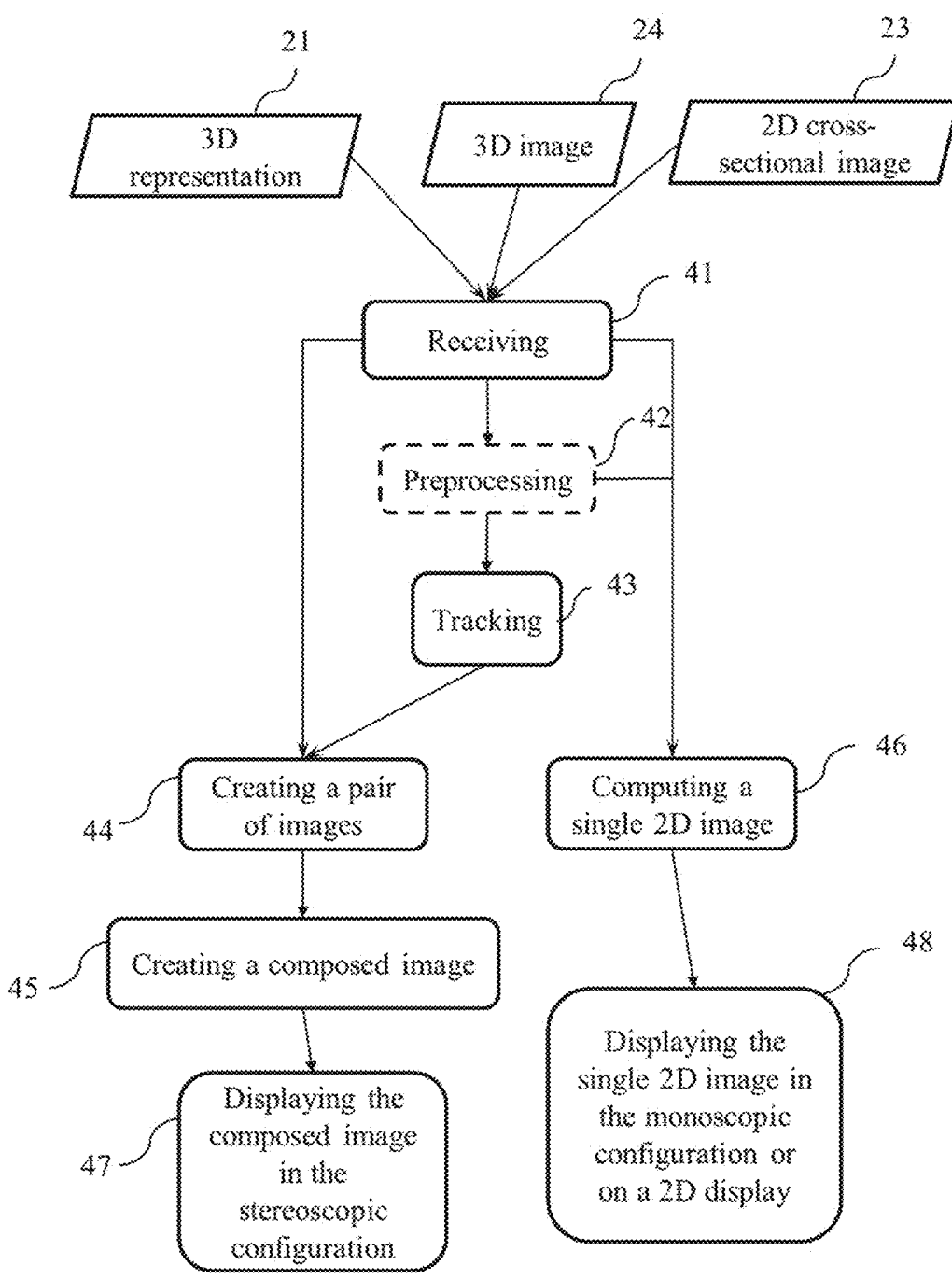
Figure 3:
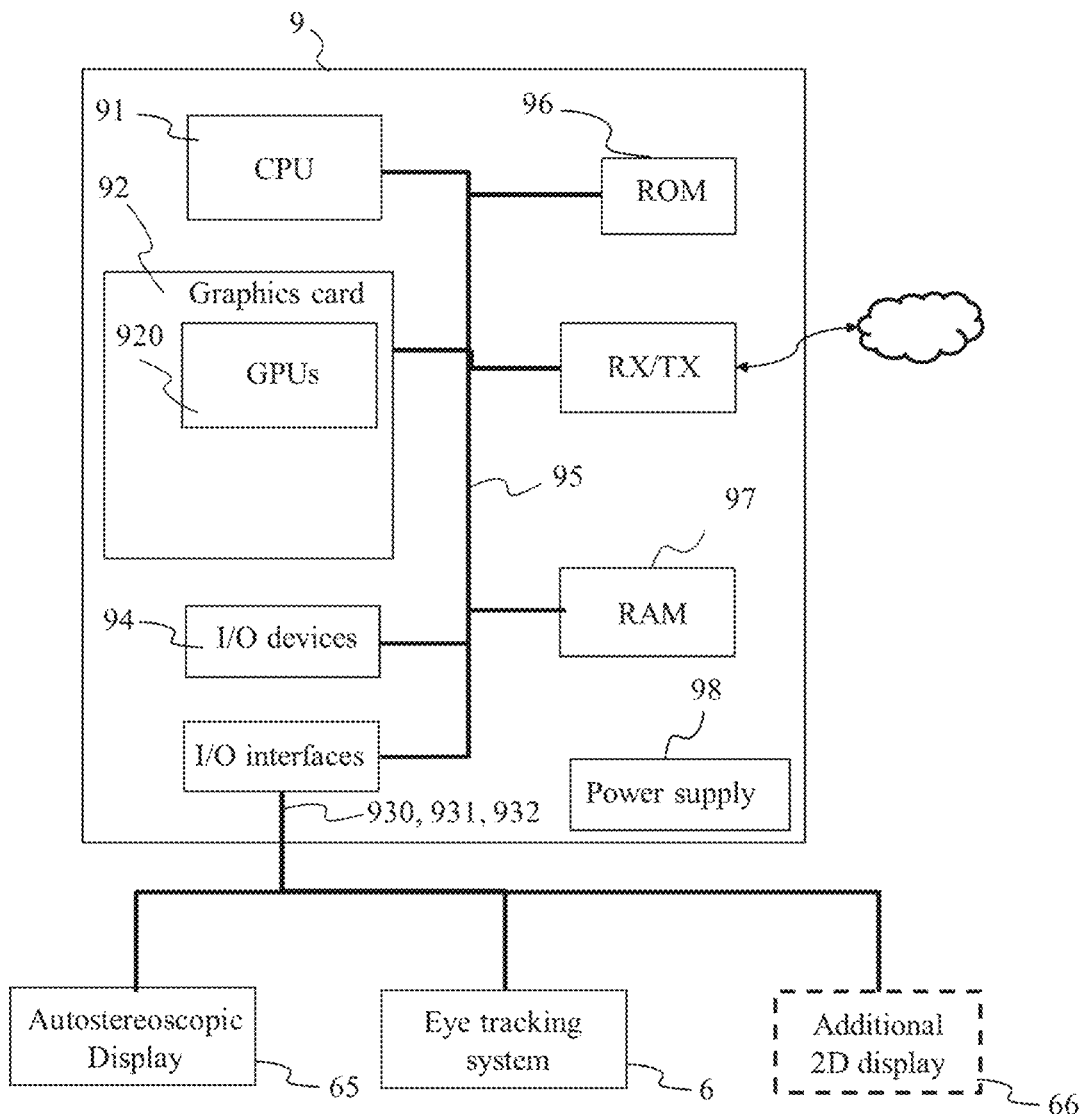
Figure 4:
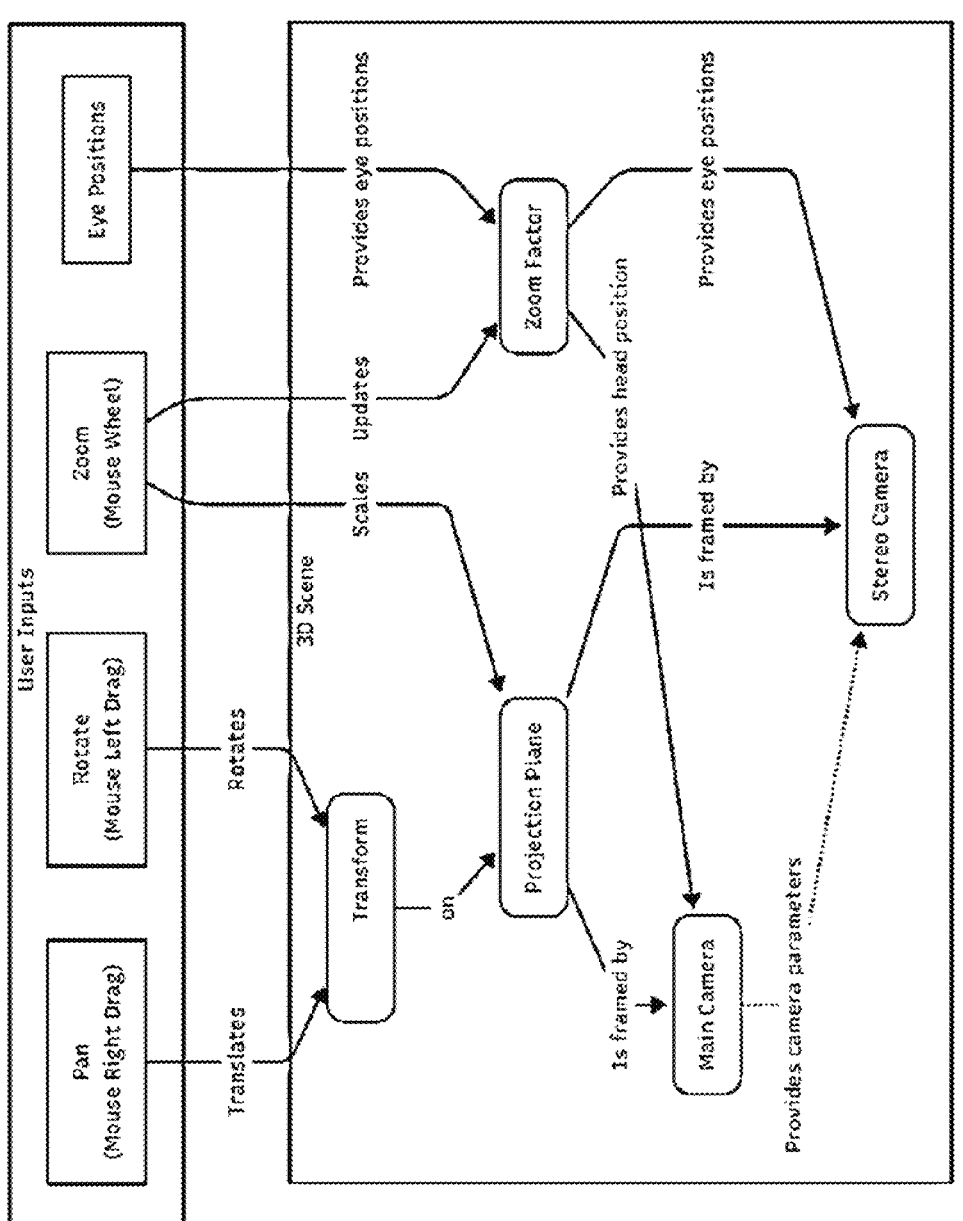
Figure 5:
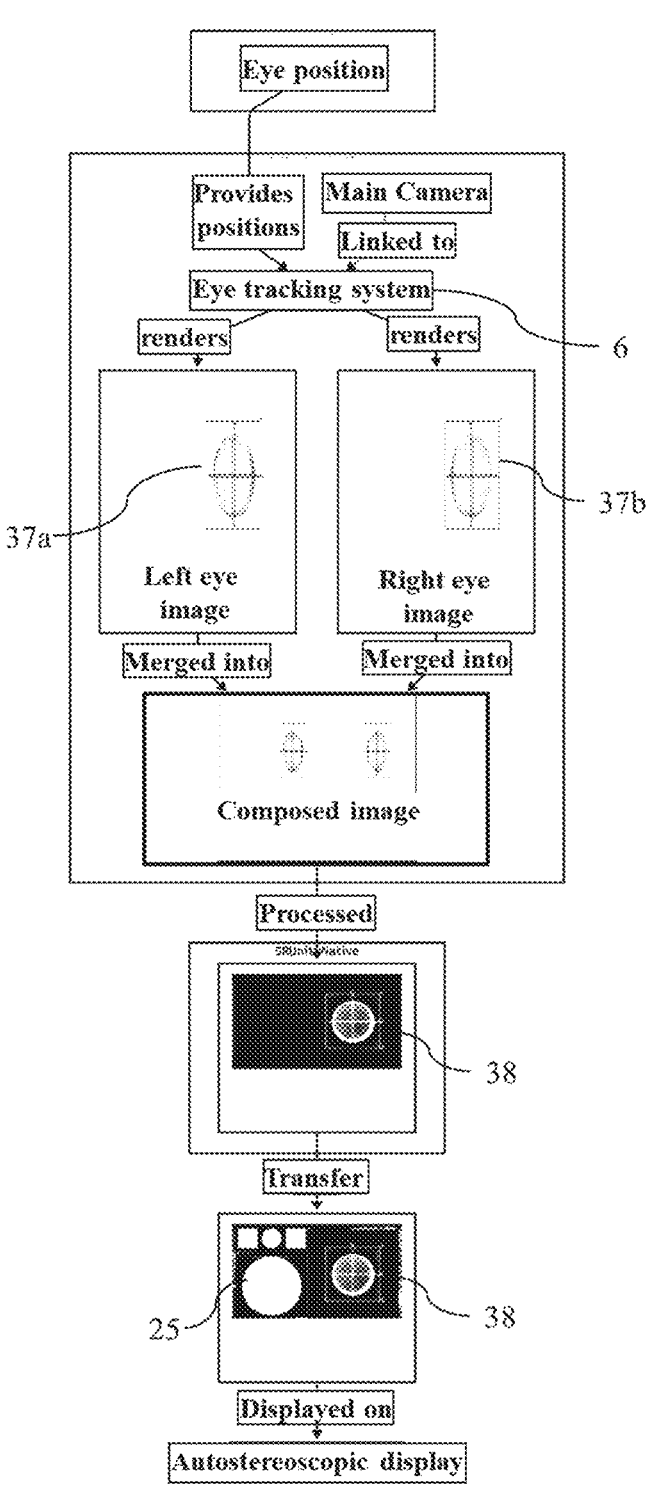
Figure 6:
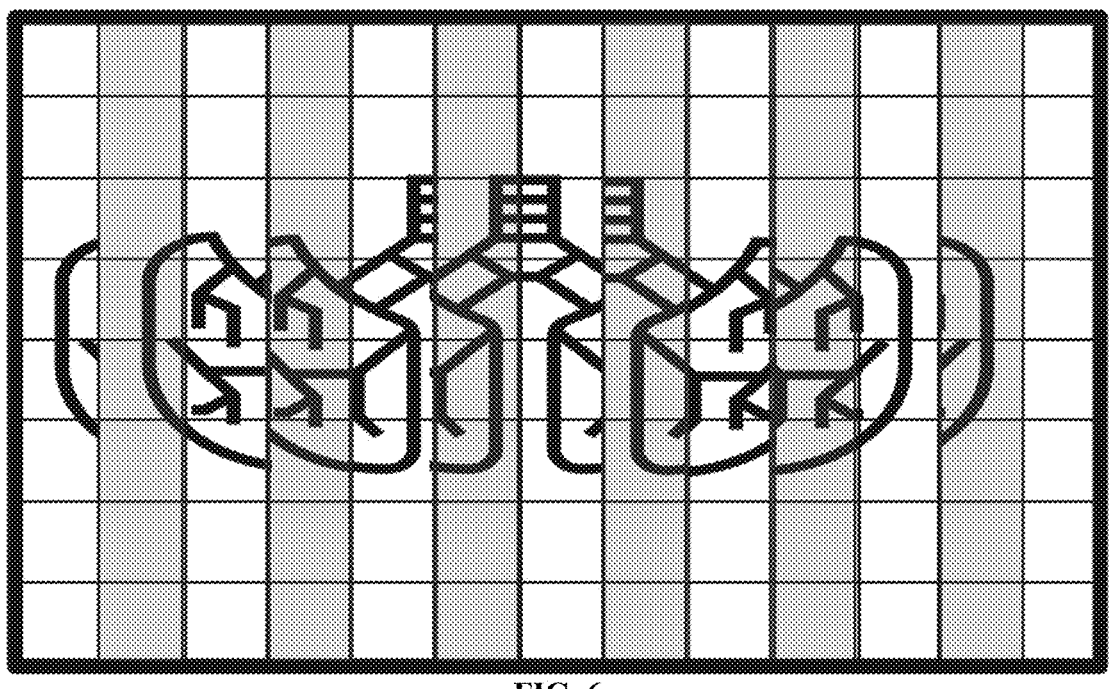
Figure 7:
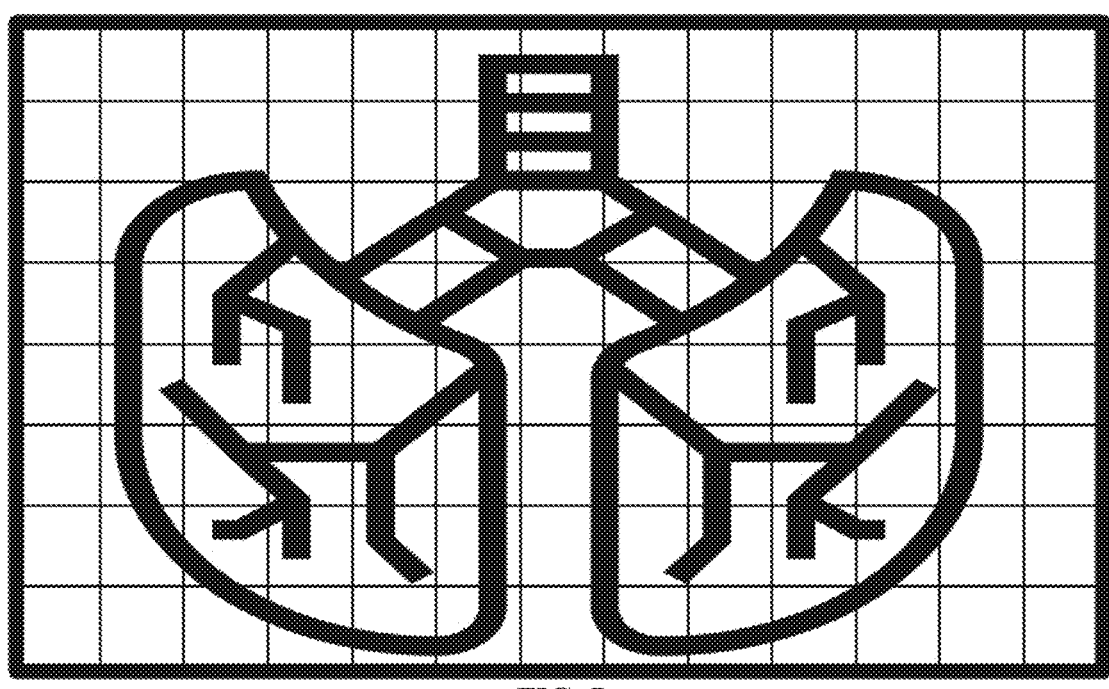

6 restrictive illustrative embodiments, the description making reference to the annexed drawings wherein:

FIG. 1 is a block diagram representing schematically a particular mode of an autostereoscopic display system for displaying a 3D and 2D representation of at least one portion of a patient, compliant with an embodiment of the present disclosure;

FIG. 2 is a flow chart showing successive steps executed with the autostereoscopic display system of FIG. 1;

FIG. 3 diagrammatically shows an apparatus integrating the functions for displaying a 3D and 2D representation of at least one portion of a patient, compliant with an embodi-ment of the present disclosure;

FIG. 4 diagrammatically shows a method for providing a perception of zoom to the user by applying a scaling transformation directly to the projection plane while also scaling the eye positions thereby changing the perception compliant with an embodiment of the present disclosure;

FIG. 5 diagrammatically shows the successive steps executed with the autostereoscopic display system of FIG. 1;

FIG. 6 shows an image displaying on the autostereoscopic display system in the stereoscopic configuration;

FIG. 7 shows an image displaying on the autostereoscopic display system in the monoscopic configuration.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its scope.

All examples and conditional language recited herein are intended for educational purposes to aid the reader in understanding the principles of the disclosure and the con-cepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embody-ing the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in associa-tion with appropriate software. When provided by a proces-sor, the functions may be provided by a single dedicated processor, a single shared processor, or a plurality of indi-vidual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

The present disclosure will be described in reference to a particular functional embodiment of an autostereoscopic display system 1, as illustrated on FIG. 1.

The autostereoscopic display system 1 comprises a switchable autostereoscopic display or screen 65 to be used in a computer-implemented method for displaying a 3D and a 2D representation of at least one portion of a patient.

The autostereoscopic display 65 allows a glasses-free depth rendering. Autostereoscopic screens 65 integrate two visual effects to create immersive, 3D experiences: parallax and stereoscopy.

Stereoscopy creates depth perception by presenting two slightly different images-one to each eye of a user-captured or rendered from viewpoints separated roughly by the inter-pupillary distance. The user's head or eye positions with respect to the subject or object to be observed are determined and the scene to be displayed is created from that viewpoint as if a camera shooting the scene is positioned at the eyes or head position. Because each eye sees the scene from a slightly different position, the brain of the user compares corresponding features and computes the disparities between them. It interprets these disparities as depth, fusing the two images into a single 3D percept in which nearer objects have larger disparities and farther objects have smaller ones. This allows a depth rendering to be provided.

The autostereoscopic display 65 has a total number of K pixels, arranged in a matrix of H×L pixels (thus H×L=K). The autostereoscopic display system 1 is configured to display 2×N pixels on the autostereoscopic display 65, arranged in a matrix of h×l pixels with h smaller than or equal to H and l smaller than or equal to L. Hence, 2×N is smaller than or equal to K.

The autostereoscopic display 65 is configured to display sequentially a plurality of image frames at a frequency equal to the native refresh rate of the display.

The autostereoscopic display 65 comprises for example an optical lens layer, each pixel being associated to a lens. In the switchable autostereoscopic display 65, the optical lens layer can be electronically switched on or off. When switched on, the optical lens layer directs the light from some pixels to the left eye of a viewer and from other pixels to the right eye of the viewer. When switched off, the lenses do not deviate the light from the pixels so that the light of all pixels is directed to both eyes of the viewer. Therefore, the switchable autostereoscopic display 65 is able to switch between at least one stereoscopic configuration while the optical lens layer is electronically switched on and a monoscopic configuration while the optical lens layer is electronically switched off.

Preferably, the position of each eye of the user relative to the autostereoscopic display 65 is determined when the switchable autostereoscopic display 65 is in the stereoscopic configuration.

The autostereoscopic display system 1 further comprises a processor configured for performing at least one of the steps of the method described in this disclosure.

The autostereoscopic display system 1 further comprises an input for receiving a 3D representation 21 of at least one portion of a patient. The 3D representation 21 of at least one portion of a patient may be computed by applying a rendering technique—for example volume rendering, point cloud, or surface rendering-on a 3D image 24 of the at least one portion of a patient. The computation of the 3D representation 21 may be performed by the processor of the autostereoscopic display system 1 or by a processor comprised in an external device. Ray-based rendering using a ray-based algorithm is a powerful method particularly useful for visualizing anatomical structures in 3D medical data, such as organs, tissues, and other internal parts. The technique may involve casting rays from a virtual viewpoint through each pixel of an image plane into the 3D image data. The ray casting may be performed for each viewpoint. For example, the ray casting is performed for each eye. Additionally, it may also be performed for an average viewpoint between the eyes. As each ray travels through the volume, it samples voxel values along its path. These samples are mapped to optical properties-such as color and opacity-using a transfer function. The final pixel value in the rendered image is computed by accumulating these mapped values along the ray's path, using techniques such as compositing. This process simulates light absorption, emission within the volume to generate a 2D image that visually represents the internal structures in 3D. The 3D representation 21 may be obtained using ray-based rendering algorithms, such as ray casting or ray tracing.

The 3D representation 21 and/or the 3D image 24 may be stored in one or more local or remote database(s) 10. The database 10 can take the form of storage resources available from any kind of appropriate storage means, which can be notably a RAM or an EEPROM (Electrically-Erasable Programmable Read-Only Memory) such as a Flash memory, possibly an SSD (Solid-State Disk).

To produce the 3D images 24, an MRI machine, a PET machine or a CT scan machine acquires a series of 2D cross-sectional images (slices) of the at least one portion of a patient representing thin cross-sections of the at least one portion of a patient. These slices are usually stacked together and are captured consecutively at different locations and orientations (like sagittal, coronal, or axial views). The slices are then stacked together to form the 3D image 24. Each slice becomes a layer in the volume and the pixels become voxels.

The autostereoscopic display system 1 may comprise a module 102 for receiving the 3D representation 21 or for receiving the 3D images 24 used to compute the 3D representation 21.

The autostereoscopic display system 1 optionally further comprises a module 105 for preprocessing the received 3D image 24 or 2D cross-sectional images 23. The module 105 may notably be adapted to standardize the received 3D image 24 or 2D cross-sectional images 23 for sake of efficient and reliable processing. This may enhance the efficiency of the downstream processing by the autostereoscopic display system 1. Such a standardization may be particularly useful when exploited images originate from different sources, including possibly different imaging systems. The module 105 may transform the 3D image 24 or 2D cross-sectional images 23, e.g. by image decompression. The module 105 may also extract attributes from the 3D image 24 or 2D cross-sectional images 23. It may align these slices accurately before reconstruction of the 3D image 24. It may comprise filtering such as Gaussian filtering or denoising the slices to improve image quality.

The frame to be displayed comprises the visualization of a 3D representation of at least one portion of a patient. A scene coordinate system may be attached to the 3D representation 21. A frame can be computed either for the stereoscopic configuration or for the monoscopic configuration.

The autostereoscopic display system 1 may comprise a module 120 for creating a composed image using the method schematically represented in FIG. 5.

To do so, the autostereoscopic display system 1 may comprise a module 110 for determining the user's head or eye positions. A pair of images is first computed. Each image (37a, 37b) of the pair of images is computed based on the 3D representation 21 as viewed from two basic (for example pre-defined) virtual positions of the two eyes of a user with respect to the 3D representation, i.e., as if cameras shooting the 3D representation 21 are positioned at the said two basic (for example pre-defined) virtual positions. This thus provides two slightly different images: one computed for each virtual eye position. Each image (37a, 37b) of the pair of images is composed of N pixels. A composed image 38 is then created by combining the pixels of the images (37a, 37b) of the pair of images.

In some examples, the module 110 is configured for tracking the position of the user's eyes or head with respect to the autostereoscopic display 65, i.e. determining a change of the position compared to the basic virtual position. This is advantageous since, when the user's head moves left or right, or up or down, the rendered viewpoint shifts accordingly, producing a pronounced motion parallax; the perspective is updated in real time, creating a vivid sense of depth.

To track eyes or head position of the user, an eye tracking system 6 configured for real-time tracking of position of each eye of a user may be used. The eye tracking system 6 may be part of the autostereoscopic display system 1. For example, the eye tracking system 6 comprises at least one tracking camera. In one embodiment, the tracking camera is a camera rig preferably comprising at least two front-facing camera lenses configured to simultaneously capture a stereoscopic video of the user, more particularly of the eyes of the user. In one embodiment, the tracking camera comprises two front-facing cameras configured to simultaneously capture a stereoscopic video of the user, more particularly of the eyes of the user. Preferably, real-time tracking of position of each eye of a user is performed when the switchable autostereoscopic display 65 is in the stereoscopic configuration. Tracking positions of the eyes of the user may be continuous.

The pair of images computed with the basic virtual position is thus updated according to the tracked position.

The positions of the user's eyes or head may be determined at the same frame rate as the frame rate of the autostereoscopic display 65. In this embodiment, the positions of the user's eyes or head is preferably determined before each frame display by the autostereoscopic display 65. The image displayed in said frame is thus computed based on the associated position of the eyes or head of the user computed for said frame.

Alternatively, the position of the user's eyes or head is determined at a predetermined tracking rate, the frame to be displayed being computed based on the position of the eyes at said tracking rate.

In the following the viewing position is the position of the user's eyes or head as being the basic virtual position of the tracked position.

The positions of the user's eyes or head (viewing positions) are determined in physical space, relative to the physical position of the autostereoscopic display 65. This thus makes it possible to determine, for each eye or for the head, a viewing position relative to autostereoscopic display 65.

The autostereoscopic display system 1 may comprise a module 130 for displaying the composed image 38 on the autostereoscopic display 65 in the stereoscopic configuration. The lenses of the display ensure that each eye of a real user only sees the image (37a, 37b) that it was rendered for. The corresponding left and right images (37a, 37b) are "targeted" to the user's left and right eyes, respectively. This process mimics natural stereoscopic vision, creating a true sense of depth and allowing the user to "look around" the composed image 38 as if the portion of the patient is physically present in front of the user.

In an embodiment, the images (37a, 37b) of the pair of images are algorithmically woven together to generate the composed image 38. Weaving effectively embeds stereoscopic information into a single composed image 38.

For example, each image (37a, 37b) of the pair of images comprises a matrix of M columns of pixels, M being a mathematical divisor of N. The composed image 38 is then created by interleaving the columns of pixels of the two images (37a, 37b) of the pair of images.

The autostereoscopic display system 1 may comprise a module 125 for providing to the user some interactions with the composed image 38.

When the autostereoscopic display 65 is in the at least one stereoscopic configuration, the 3D representation 21 of the portion of the patient may be manipulated directly within the display's projection plane. For example, by default, the composed image 38 is positioned so that its center aligns with the center of the projection plane.

In an example, it is possible to provide a perception of zoom to the user by applying a scaling transformation directly to the projection plane while also scaling the eye positions thereby changing the perception as shown in FIG. 4. The camera frustum aligns with a single slice of the projection plane. Zooming works by resizing the rectangular projection area. When the rectangle gets larger while the object stays the same size, the object appears smaller on screen. When the rectangle shrinks and the object's size doesn't change, the object appears larger. This makes the volumetric representation appear larger or smaller while its center remains anchored to the projection plane.

The autostereoscopic display system 1 may comprise a module 140 for providing, in the monoscopic configuration, a flat rendering to the user. To do so, a single 2D image composed of 2×N pixels is computed based on the 3D representation 21 of the at least one portion of a patient.

The autostereoscopic display system 1 may comprise a module 150 for displaying the single 2D image 25 using the autostereoscopic display 65 in the monoscopic configuration. Therefore, only one image is displayed and both eyes of the user see the same image. This thus provides a flat rendering to said user. Advantageously, the method of the invention allows to display, on an autostereoscopic display 65, an image at a resolution which may reach the total native resolution K of the display. In other words, the method allows to display the single 2D image 25 at a higher resolution (2N) than the resolution (N) of each of the two images of the composed image 38. This is represented in FIGS. 6 and 7: in FIG. 6, an image of an organ is displayed on the autostereoscopic display 65 in the stereoscopic configuration and in FIG. 7, an image of the same organ is displayed on the autostereoscopic display 65 in the monoscopic configuration. In FIG. 6, the displayed image is constructed by interleaving columns of pixels of a pair of images—the grey columns are for left eye while the white columns are for the right eye. It is clear that the image of FIG. 7 has a larger resolution than in FIG. 6.

In one embodiment, the autostereoscopic system 1 comprises an additional 2D display 66. In this embodiment, a 2D image may be displayed on the additional 2D display 66. For example, the single 2D image 25 computed by the method as explained above is displayed in the additional 2D display 66. This advantageously makes it possible to provide several representations simultaneously and synchronously with the display of the composed image 38 on the autostereoscopic display 65. In one embodiment, the additional 2D display 66 is a second switchable autostereoscopic display 65 configured to switch between a stereoscopic configuration and a monoscopic configuration, the 2D image being displayed on the second switchable autostereoscopic display 65 in the monoscopic configuration. The autostereoscopic display 65 and the additional 2D display 66 or the second switchable autostereoscopic display 65 may be arranged in a field of view of a single user, i.e., in the same field of view of the user.

Advantageously, the single 2D image 25 and the composed image 38 are associated to a common coordinate system, preferably the common coordinate system is the scene coordinate system.

In the preferred embodiment, this allows to provide a peer functionality leveraging at least an additional 2D display 66. In this embodiment, the single 2D image 25 is computed as viewed from an additional viewing direction, for instance a viewing direction perpendicular to the 2D display plane. In this embodiment, the composed image 38 is visible to a first viewer (for example a patient) on the autostereoscopic display 65 while the single 2D image 25 is visible to a second user (for example a physician) on the additional 2D display 66. This allows the physician to manipulate the single 2D image 25 (for example rotating, zooming, . . . ) and transpose this manipulation to the composed image 38 thanks to the common coordinate system. In this setup, the patient benefits from the autostereoscopic view, while the physician uses a standard screen which is simpler to use for image manipulation. This embodiment advantageously supports patient-physician communication.

When the single 2D image 25 and the composed image 38 are associated to a common coordinate system, the method may be performed by using a non-switchable autostereoscopic display 65 and an additional 2D display 66 as described above. Alternatively, the method may provide the peer functionality using only a switchable autostereoscopic display 65. The single 2D image 25 and the composed image 38 are thus displayed sequentially: the module 130 displays either the single 2D image 25 or the composed image 38 and the configuration of the autostereoscopic display 65 is switched to manipulate the 2D image 25 and observe the result in the composed image 38.

A module 130 of the autostereoscopic display system 1 may be further configured for displaying, using the autostereoscopic display 65 in the at least one stereoscopic configuration, a flat rendering of a cross-sectional image 23 alongside the depth rendering of the 3D representation 21. The cross-sections 23 or cross-sectional images 23 may be acquired by the MRI machine, the PET machine or CT scanner. The cross-sections 23 or cross-sectional images 23 may be the slices described hereabove. The module 102 may be configured to receive the cross-sectional images 23. The single 2D image 25 is created based on said cross-sectional image 23.

In an example, the module 140 is configured for computing twin images of the cross-sectional image 23. The twin images are, by definition, two identical images. The twin images are then combined with the pair of images forming the composed image 38. This last step may be performed by the module 140 or the module 120. The final image issued from the combining is thus a multi-rendered image which provides, when displayed using the autostereoscopic display 65 in the at least one stereoscopic configuration, two renderings (flat rendering of a cross-sectional image 23 and the depth rendering of the 3D representation 21) simultaneously to the user. Indeed, since the twin images are identical images which will be displayed to the left eye and the right eye of the user, the user will have a flat rendering (not a depth rendering) and the cross-section 23 represented by the twin image may appear as floating in the foreground of the scene. It is understood that the disclosure is not limited to this example of two renderings and that one or a plurality of pair of images forming the composed image 38 may be combined with one or a plurality of twin images.

If the number of pixels of the composed image 38 is lower than the total native resolution K of the autostereoscopic display 65, the flat rendering of the cross-sectional image 23 may be displayed next to the composed image 38 without superposition as represented in FIG. 5. To do so, the module 140 may be configured for creating, from the twin images, a composed flat image 25. For example, if the autostereoscopic display 65 has a total number of K pixels arranged in a matrix of H×L pixels, the composed image 38 may comprise $h_{3D} \times l_{3D}$ pixels and the composed flat image 25 may comprise $h_{2D} \times l_{2D}$ pixels with $h_{3D} + h_{2D}$ smaller than or equal to H or with $l_{3D} + l_{2D}$ lower than or equal to L.

In another example, the flat rendering of the cross-sectional image 23 may overlay (be superposed on) at least partially the composed image 38. For example, if the autostereoscopic display 65 has a total number of K pixels arranged in a matrix of H×L pixels, the composed image 38 may comprise $h_{3D} \times l_{3D}$ pixels and the composed flat image may comprise $h_{2D} \times l_{2D}$ pixels with $h_{3D} + h_{2D}$ greater than H and/or $l_{3D} + l_{2D}$ greater than L. In this embodiment, at least part of the pixels values of the composed image 38 are replaced by the values of the superposed pixels of the twin images. The final image resulting from the superposition of the flat rendering of the cross-sectional image 23 over the composed image 38 comprises $h_{final} \times l_{final}$ pixels with $h_{final}$ smaller than or equal to H and $l_{final}$ smaller than or equal to L.

When the flat rendering of the cross-sectional image 23 and the composed image 38 are associated to a common scene coordinate system, the autostereoscopic display system 1 may comprise a module (125, 145) configured for providing to the user some interactions with either the composed image 38 or the flat rendering of the cross-sectional image 23 implying an update of the display with the non-interacted image. The viewer of the composed image 38 (for example the patient) thus has a direct perception of the result of a modification in a representation of the anatomy with perception of depth, while the viewer of the flat rendering of the cross-sectional image 23 (for example the physician) is interacting with the single 2D image 25 and a standard User Interface (UI). There is thus no need to change the habits of the user in exploring the 2D slices, placing landmarks or measuring, but the result can be seen with a true perception of space, which for instance provides a better understanding of various anatomical elements.

For example, at least one pixel may be selected within the flat rendering of the cross-sectional image 23.

The selection of at least one pixel within the flat rendering of the cross-sectional image 23 may comprise automatically selecting a set of pixels comprising a primary pixel selected by the user and at least one neighboring pixel. In this embodiment, the module 125 is configured for:

computing a pair of updated images wherein the set of pixels are highlighted, each updated image of the pair of images being computed based on said 3D representation 21 viewed from each viewing position, each updated image of the pair of updated images comprising N pixels;

creating, using the pair of updated images, a composed updated image by combining the pixels of the two updated images of the pair of updated images;

displaying the composed updated image using the autostereoscopic display 65 in the stereoscopic configuration;

and optionally the module 145 is configured for:

computing a single 2D updated image based on said 3D representation 21 wherein the set of pixels are highlighted, the single 2D updated image comprising 2×N pixels;

displaying the single 2D updated image using the autostereoscopic display 65 in the monoscopic configuration.

To ease the interaction of the user with the flat rendering of the cross-sectional image 23 to select the pixels, a representation of a cursor may be displayed over the flat rendering of the cross-sectional image 23 for example by modifying pixel values of the flat rendering of the cross-sectional image 23 at the position of the representation of the cursor. The position of the representation of the cursor may be provided based on an input device 94 such as for example a keyboard, a mouse, a trackball, a webcam connected to the autostereoscopic display system 1.

According to an example of updating the composed image 38, when the 3D representation 21 is computed by applying a volume rendering technique on a 3D image 24, the module 125 is configured for generating the 3D representation 21 by modifying the parameters of volume rendering technique based on said selection of pixels. In the 3D representation 21, the voxels are mapped to optical properties-such as color and opacity-using a transfer function. During the ray-based rendering, each pixel in the final rendered image corresponds to the accumulated result of sampling and compositing the voxel values along a ray path. The voxel values from the 3D representation 21 are transformed through a transfer function that assigns specific colors and opacities based on their intensity. The module 125 is thus configured to modify the parameters of the transfer function based on the selected pixels therefore providing a modified rendering to the user. This advantageously allows selective emphasis of particular anatomical features. This embodiment is advantageous since a preview of the pixel selection and its effect on the result of the ray-based algorithm may be displaying in real-time in the composed updated image the result before choosing, by the user, the final transfer function. This is particularly advantageous when the flat rendering of the cross-sectional image 23 where the pixel selection happens and the depth rendering of the 3D representation are in the same field of view of the user, whether the flat rendering of the cross-sectional image 23 is displayed on a fraction of the autostereoscopic display 65 or on the additional 2D display 66.

According to another example of updating the composed image 38, the module 125 is configured for highlighting (for example using a different color) the pixels of the composed updated image (therefore generating the updated composed image) corresponding to the pixels selected in the single 2D image 25. The single 2D image 25 may also be updated using the module 145 by highlighting the selected pixels.

According to another example of updating the composed image 38, the module 125 is configured for adding, in the composed image 38, a graphical element by:

computing a pair of updated images comprising the graphical element, each updated image of the pair of images being computed based on said 3D representation 21 viewed from each viewing position, each updated image of the pair of updated images being composed of N pixels;

creating, using the pair of updated images, a composed updated image by combining the pixels of the two updated images of the pair of updated images;

displaying the composed updated image using the autostereoscopic display 65 in the stereoscopic configuration;

and optionally the module 145 is configured for:

computing a single 2D updated image based on said 3D representation 21 comprising the graphical element, the single 2D updated image being composed of 2×N pixels;

displaying the single 2D updated image using the autostereoscopic display 65 in the monoscopic configuration.

For example, when two pixels are selected, the graphical element may be a representation of a 3D distance or a projected distance between said two pixels. In another example, when three pixels or four pixels are selected, the graphical element may be a representation of a 3D angle or a projected angle between two lines, each line extending between two of the selected pixels.

In its automatic actions, the autostereoscopic display system 1 may for example execute the following process (FIG. 2):

Receiving 41 the 3D representation 21 of at least one portion of a patient and/or the 3D images 24 and/or the cross-sectional images 23;

Optionally preprocessing 42 the 3D representation 21, and/or the 3D images 24, and/or the cross-sectional images 23;

Tracking 43 a viewing position of each eye of a user in real-time with respect to the autostereoscopic display 65;

Computing 44 a pair of images, each image of the pair of images being computed based on said 3D representation 21 viewed from each viewing position, each image of the pair of images comprising N pixels;

Creating 45, using said pair of images, a composed image 38 by combining the pixels of the images of the pair of images;

Computing 46 a single 2D image 25 composed of 2×N pixels based on said 3D representation 21;

Displaying 47 the composed image using the autostereoscopic display 65 in the stereoscopic configuration thereby creating a depth rendering of the composed image 38 to said user;

Displaying 48 the single 2D image 25 using the autostereoscopic display 65 in the monoscopic configuration thereby providing a flat rendering to the user at a higher resolution than the composed image 38.

A particular apparatus 9, visible on FIG. 3, is embodying the processor of the autostereoscopic display system 1 described above. It corresponds for example to a workstation, a laptop, a tablet, a smartphone, That apparatus 9 is suited to image generation of at least one portion of a patient with a depth rendering and a flat rendering at higher resolution. It comprises the following elements, connected to each other by a bus 95 of addresses and data that also transports a clock signal:

a microprocessor 91 (or CPU);

a graphics card 92 comprising one or several several Graphical Processing Units (or GPUs) 920; the GPUs are quite suited to image processing, due to their highly parallel structure; for example the graphics card is an NVIDIA Geforce RTX 20-Series™ card;

a non-volatile memory of ROM type 96;

a RAM 97;

one or several I/O (Input/Output) devices 94 such as for example a keyboard, a mouse, a trackball, a webcam, a microphone; other modes for introduction of commands such as for example vocal recognition are also possible;

a wireless or wired data communication unit (RX/TX) such as a WIFI module for example;

a power supply 98.

According to a variant, the power supply 98 is external to the apparatus 9.

CPU and GPU cores may be combined on the same die by an Accelerated Processing Unit (APU).

The apparatus 9 may comprise a USB or a HDMI port 931 for connecting the eye tracking system 6. The apparatus 9 may comprise a display port 930 for connecting the switchable autostereoscopic display 65. The apparatus 9 may comprise a further display port 932 for connecting the additional 2D display.

The apparatus 9 be configured to position a colored spot indicator at the surface of the composed image 38.

The apparatus 9 may be configured to analyze the hand gestures of the user, so has to offer an intuitive user interface to manipulate the composed image 38 in the stereoscopic configuration.

The Input/Output devices 94 may comprise a 3D controller, such as a 3D pen, the position of the 3D controller being detected and analyzed by the processor, so as to offer an intuitive user interface to manipulate the 3D model in the stereoscopic configuration.

It is noted that the word "register" used hereinafter in the description of memories 97 can designate in each of the memories mentioned, a memory zone of low capacity (some binary data) as well as a memory zone of large capacity (enabling a whole program to be stored or all or part of the data representative of data calculated or to be displayed). Also, the registers represented for the RAM 97 and can be arranged and constituted in any manner, and each of them does not necessarily correspond to adjacent memory locations and can be distributed otherwise (which covers notably the situation in which one register includes several smaller registers).

When switched-on, the microprocessor 91 executes the instructions of the program contained in the ROM and/or in the RAM 97.

As will be understood by a skilled person, the presence of the graphics card 92 is not mandatory, and can be replaced with entire CPU processing and/or simpler visualization implementations.

What is claimed is:

1. A computer-implemented method for displaying, on an autostereoscopic display system comprising a switchable autostereoscopic display, an image based on a 3D representation of at least one portion of a patient, said switchable autostereoscopic display configured to display at least 2×N pixels and being adapted to be switched between at least one stereoscopic configuration and a monoscopic configuration, said method comprising:

receiving a 3D representation of at least one portion of a patient;

determining if the autostereoscopic display is to operate in the stereoscopic configuration or in the monoscopic configuration, and:

if the autostereoscopic display is determined to operate in the stereoscopic configuration, switching the autostereoscopic display to the stereoscopic configuration, and:

determining, for each eye of a user, a viewing position of said eye relative to the autostereoscopic display;

computing a pair of 2D images, each 2D image of the pair of 2D images being computed based on said 3D representation viewed respectively from each viewing position, each 2D image of the pair of 2D images being composed of N pixels;

creating, using said pair of 2D images, a composed image by combining the pixels of the 2D images of the pair of 2D images;

displaying said composed image on the autostereoscopic display in the at least one stereoscopic configuration thereby providing a depth rendering of the composed image to said user;

if the autostereoscopic display is determined to operate in the monoscopic configuration, switching the autostereoscopic display to the monoscopic configuration, and:

computing a single 2D image composed of 2×N pixels based on said 3D representation;

displaying the single 2D image on the autostereoscopic display in the monoscopic configuration thereby providing a flat rendering of the at least one portion of the patient to said user at a higher resolution than the composed image.

2. The method according to claim 1, further comprising, when the autostereoscopic display is switched to operate in the stereoscopic configuration, tracking positions of the eyes of the user to determine, for each eye, the viewing position of said eye relative to the autostereoscopic display over time, wherein the composed image is repeatedly updated and displayed according to changes in the viewing position of each eye relative to the autostereoscopic display.

3. The method according to claim 1 wherein, the single 2D image is computed and displayed on an additional 2D display comprised in the autostereoscopic system, the computing and the displaying of the single 2D image being simultaneous and synchronous with the computing and the displaying of the composed image on the autostereoscopic display.

4. The method according to claim 1 further comprising displaying on the autostereoscopic display in the at least one stereoscopic configuration, a flat rendering of a cross-sectional image associated to the 3D representation alongside the depth rendering of the 3D representation.

5. The method according to claim 4 wherein displaying a flat rendering of a cross-sectional image comprises:

receiving a cross-sectional image associated to said 3D representation of at least one portion of a patient;

computing twin images of the cross-sectional image;

computing a multi-rendered image by combining said twin images of the cross-sectional image and the pair of images forming the composed image;

displaying the multi-rendered image using the autostereoscopic display in the at least one stereoscopic configuration.

6. The method according to claim 5 wherein the selection of at least one pixel within the flat rendering of the cross-sectional image comprises automatically selecting a set of pixels comprising the pixel selected using the cursor and at least one neighboring pixel, the method further comprising:

computing a pair of updated images wherein the set of pixels are highlighted, each updated image of the pair of images being computed based on said 3D representation viewed from each viewing position, each updated image of the pair of updated images comprising N pixels;

creating, using the pair of updated images, a composed updated image by combining the pixels of the two updated images of the pair of updated images;

displaying the composed updated image on the autostereoscopic display in the stereoscopic configuration; and optionally:

computing a single 2D updated image based on said 3D representation wherein the set of pixels are highlighted, the single 2D updated image comprising 2×N pixels;

displaying the single 2D updated image on the autostereoscopic display in the monoscopic configuration.

7. The method according to claim 4 wherein displaying a flat rendering of a cross-sectional image comprises:

receiving a cross-sectional image associated to said 3D representation of at least one portion of a patient;

computing twin images of the cross-sectional image;

creating, from the twin images, a composed flat image which, when displayed on the autostereoscopic display in the at least one stereoscopic configuration provides the flat rendering to the user;

displaying the composed image next to the composed flat image on the autostereoscopic display in the at least one stereoscopic configuration.

8. The method according to claim 4 wherein the flat rendering of the cross-sectional image and the composed image are associated to a common scene coordinate system, the method further comprising:

displaying, over the flat rendering of the cross-sectional image, a representation of a cursor, and updating, upon selection with said cursor of at least one pixel within the flat rendering of the cross-sectional image, the composed image based on selected pixels by:

computing a pair of updated images, each updated image of the pair of updated images being computed based on said 3D representation viewed from each viewing position, each updated image of the pair of updated images being composed of N pixels;

creating, using the pair of updated images, a composed updated image by combining the pixels of the two updated images of the pair of updated images;

displaying the composed updated image on the autostereoscopic display in the stereoscopic configuration; and optionally:

computing a single 2D updated image composed of 2×N pixels based on said 3D representation;

displaying the single 2D updated image on the autostereoscopic display in the monoscopic configuration.

9. The method according to claim 8 wherein updating the composed image comprises adding, in the composed image, a graphical element by:

computing a pair of updated images comprising the graphical element, each updated image of the pair of updated images being computed based on said 3D representation viewed from each viewing position, each updated image of the pair of updated images being composed of N pixels;

creating, using the pair of updated images, a composed updated image by combining the pixels of the two updated images of the pair of updated images;

displaying the composed updated image on the autostereoscopic display in the stereoscopic configuration;

and by optionally:

computing a single 2D updated image based on said 3D representation comprising the graphical element, the single 2D updated image being composed of 2×N pixels;

displaying the single 2D updated image on the autostereoscopic display in the monoscopic configuration.

10. The method according to claim 9 wherein two pixels are selected and wherein the graphical element is a representation of a 3D distance between said two pixels.

11. The method according to claim 8 wherein the 3D representation of at least one portion of a patient is computed by applying a volume rendering technique on a 3D image of the at least one portion of the patient, and wherein updating the composed image comprises generating the 3D representation by modifying parameters of the volume rendering technique based on said selection of at least one pixel within the flat rendering of the cross-sectional image.

12. A non-transitory program storage device, readable by a computer, tangibly embodying a program of instructions executable by the computer to perform a method according to claim 1.

13. An autostereoscopic display system comprising:

a switchable autostereoscopic display configured to display 2×N pixels and able to switch between at least one stereoscopic configuration and a monoscopic configuration;

an eye tracking system configured for real-time tracking of a viewing position of each eye of a user;

an input for receiving a 3D representation of at least one portion of a patient;

a processor configured for:

computing a pair of images, each image of the pair of images being computed based on said 3D representation viewed respectively from each viewing position, each image of the pair of images being composed of N pixels;

creating, using said pair of images, a composed image by combining the pixels of the images of the pair of images;

computing a single 2D image comprising 2×N pixels based on said 3D representation;

an output configured for:

displaying the composed image on the autostereoscopic display in the stereoscopic configuration thereby creating a depth rendering of the composed image to said user;

displaying the single 2D image on the autostereoscopic display in the monoscopic configuration thereby providing a flat rendering to the user at a higher resolution than the composed image.

14. The autostereoscopic display system according to claim 13 further comprising a 2D display configured for displaying the single 2D image.

15. The autostereoscopic display system according to claim 14, wherein the autostereoscopic display and the 2D display can be arranged to be both in a field of view of a single user.

* * * * *